United States Patent [19]
Sharber et al.

[11] Patent Number: 6,075,180
[45] Date of Patent: Jun. 13, 2000

[54] CARVABLE PTFE IMPLANT MATERIAL

[75] Inventors: Norman J. Sharber, Flagstaff; Kenneth W. Moll, Camp Verde; Karl E. Schwarz; Clayton M. Sparling, both of Flagstaff, all of Ariz.

[73] Assignee: W. L. Gore & Associates, Inc., Newark, Del.

[21] Appl. No.: 08/900,060

[22] Filed: Jul. 24, 1997

Related U.S. Application Data

[60] Continuation of application No. 08/518,132, Aug. 22, 1995, abandoned, which is a division of application No. 08/198,797, Feb. 17, 1994, abandoned.

[51] Int. Cl.[7] .................................................. A61F 2/02
[52] U.S. Cl. ............................ 623/11; 623/13; 623/66; 606/76
[58] Field of Search ............................... 623/11, 13, 66; 606/76

[56] References Cited

U.S. PATENT DOCUMENTS

| | | | |
|---|---|---|---|
| 2,833,686 | 5/1958 | Sandt | 154/139 |
| 4,816,339 | 3/1989 | Tu et al. | 623/1 |
| 5,093,179 | 3/1992 | Scantlebury et al. | 433/215 |
| 5,098,779 | 3/1992 | Kranzler et al. | 623/11 |
| 5,433,996 | 7/1995 | Kranzler et al. | 623/11 |
| 5,718,973 | 2/1998 | Lewis et al. | 623/11 |

*Primary Examiner*—Paul B. Prebilic
*Attorney, Agent, or Firm*—Wayne D House

[57] ABSTRACT

A carvable implant material for use in surgery and especially in plastic and reconstructive surgery. At least two layers of porous PTFE (polytetrafluoroethylene) sheet material are laminated together by an adhesive placed between the adjacent layers of porous PTFE sheet material. Alternatively, a plurality of discrete pieces of porous PTFE may be adhered together by an adhesive. The presence of the adhesive provides a significant increase in stiffness and hence in carvability beyond that possible in a single layer of porous PTFE without the adhesive. Preferred adhesives are thermoplastic fluoropolymers of lower crystalline melt temperature than PTFE, such as FEP or PFA.

15 Claims, 2 Drawing Sheets

CARVABLE PTFE IMPLANT MATERIAL

This application is a continuation of application Ser. No. 08/518,132 filed Aug. 22, 1995 now abandoned which is a division of Ser. No. 08/198,797 filed Feb. 17, 1994 which is now abandoned.

FIELD OF THE INVENTION

This invention relates to a carvable porous polytetrafluoroethylene implant material for use in plastic and reconstructive surgery and to a method for making the implant material.

BACKGROUND OF THE INVENTION

Plastic and reconstructive surgery often requires the use of graft materials for the replacement or augmentation of tissues. Materials used for this purpose heretofore have been of biologic or synthetic origin. Biologic materials of both autologous and homologous origin have been tried extensively. Both types of biologic material have been subject to unpredictable resorption, requiring the patient to undergo additional corrective surgery. The use of homologous implant materials, for example, collagen or bone, can also result in an adverse immunologic reaction that can lead to graft rejection and extrusion of the implant material. While such adverse reactions do not occur with autologous implants, the use of autologous material involves additional surgical time and trauma for their removal.

Synthetic materials previously used for implantation have generally been polymeric, for example, silicone and polytetrafluoroethylene (hereinafter PTFE). Non-porous materials do not allow tissue ingrowth and as a consequence are known to migrate from the implant location. Preferred synthetic materials have a porous structure that promotes tissue ingrowth and stabilization of the implanted material.

Proplast® (Vitek, Inc. Houston, Tex.), a carvable porous composite implant material comprising PTFE fibers, powdered PTFE resin and carbon or aluminum oxide, has been used previously as an implantable material for reconstructive surgery. This material and its methods of manufacture are described in U.S. Pat. Nos. 3,992,725 and 4,129,470. The manufacturing procedure involves blending the above listed materials with a soluble filler, filtering the blend to produce a cake, pressing and heating the cake, drying the cake, sintering the cake, and finally leaching out the filler material and again drying the resulting porous composite. The finished material was claimed to be carvable and to allow tissue ingrowth. However, the use of carbon or aluminum oxide in this material increases its tissue reactivity, potentially resulting in undesirable complications such as encapsulation by fibrous tissue, erosion of overlying tissues and extrusion. Finally, the carbon impregnated material is often visible through the skin when implanted subcutaneously in light-skinned patients.

PTFE without other added materials such as carbon has a long history of use as an implantable material because it is one of the least reactive materials known. In porous form it can allow tissue ingrowth. Porous PTFE has been available for some time in a form known as expanded PTFE. The manufacture of this material is described in U.S. Pat. Nos. 3,953,566, 3,962,153 and 4,187,390. Expanded PTFE has a microstructure characterized by nodes interconnected by fibrils. This material has a history of use in such implant applications as vascular grafts, sutures and structural soft tissue repair such as hernia repair. The porosity and microstructure of expanded PTFE can be varied to produce different permeability characteristics for use in a variety of applications.

U.S. Pat. No. 5,098,779 by the present inventors describes a carvable, implantable porous PTFE material wherein the PTFE is made carvable by a coating or impregnation of a biodegradable stiffening agent. While this is an effective means of providing carvability in porous PTFE, the coating can interfere with the porosity and tissue ingrowth characteristics of the surface of the porous PTFE until enough of the stiffening agent has been absorbed by the surrounding tissue.

SUMMARY OF THE INVENTION

The present invention is a carvable implant material for use in surgery and especially in plastic and reconstructive surgery. The material comprises at least two layers of porous PTFE sheet material laminated together by an adhesive. The presence of the adhesive provides a significant increase in stiffness and hence in carvability beyond that possible in porous PTFE alone. Preferred adhesives are thermoplastic fluoropolymers of lower crystalline melt temperature than PTFE, such as FEP or PFA. In an alternative embodiment a plurality of discrete pieces of porous PTFE, such as shredded porous PTFE, may also be adhered together to make a cork-like material that is useful as a carvable implant material.

DETAILED DESCRIPTION OF THE INVENTION

The ideal material for use in plastic and reconstructive surgery must be biocompatible and should be porous to allow tissue attachment and ingrowth to prevent migration of the material. It would have a texture similar to living tissue so that the implanted material does not feel discontinuous with the surrounding tissue. Finally, it must be capable of being readily shaped to the desired contour.

Pure, porous PTFE possesses all of the above attributes with the exception of the ability to be readily shaped. It cannot be shaped by compression as the porosity and tissue ingrowth characteristic of the material will be severely compromised. The inherent softness of this material makes it very difficult to carve to a desired shape.

Carvable is herein intended to mean capable of being carved to a desired shape with the use of a sharp blade. Porous PTFE typically compresses under the pressure of a sharp blade and so does not lend itself to being carved. It has been found possible to render porous PTFE carvable by laminating porous PTFE sheets together with an adhesive. The adhesive renders the porous PTFE adequately rigid for carving.

Figure 1:
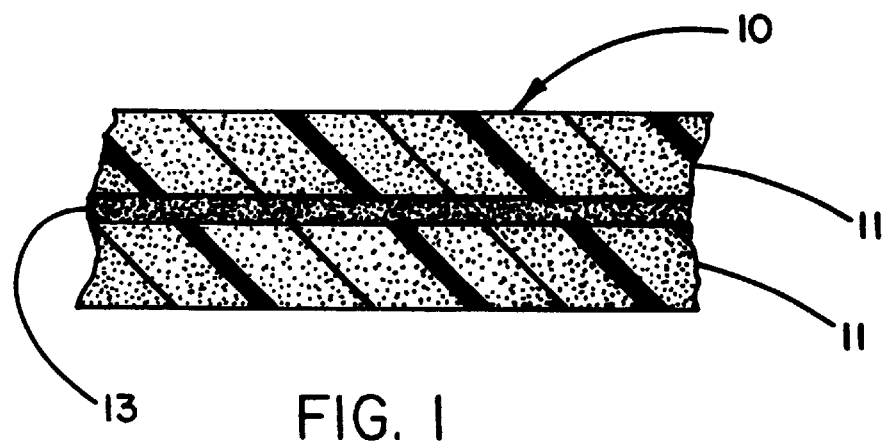
FIG. 1 describes a cross section of the implant material of the present invention showing two layers of porous PTFE sheet material laminated together by an adhesive.

FIG. 1 describes a cross section of the carvable implant material 10 of the present invention wherein porous PTFE sheets 11 are laminated together by an adhesive 13. The adhesive is preferably a thermoplastic and more preferably a thermoplastic fluoropolymer having a lowered crystalline melt temperature than PTFE, such as fluorinated ethylene propylene (hereinafter FEP) or perfluoroalkoxy (hereinafter PFA). Preferably the adhesive is in the form of a sheet material. A preferred method of forming the implant material is by stacking alternate layers of porous PTFE sheet material and sheets of the thermoplastic adhesive. Pressure and heat are applied to the stack with the pressure applied normal to the surfaces of the sheets. The heat must be in excess of the melt temperature of the adhesive sheets to cause the adhesive sheet to soften and penetrate into the porous surface of the porous PTFE sheets, thereby causing the porous PTFE sheets to become adhered together when the heat and pressure are removed. The heat should be removed first so that the adhesive is able to harden prior to removal of the pressure.

Alternatively, the adhesive may be applied in the form of a liquid if enough of the appropriate adhesive is used to result in a carvable laminate. For example, multiple coats of Teflon® FEP 120 Aqueous Dispersion (DuPont de Nemours, Wilmington, Del.) wherein each individual coat is allowed to dry before the application of the successive coat, can be applied to one or both surfaces of the porous PTFE sheet material prior to stacking. Pressure and heat appropriate to melt the Teflon FEP 120 Aqueous Dispersion are then applied to the stack. The resulting laminate is carvable if there is enough FEP between adjacent layers of porous PTFE to provide the increased stiffness necessary for carvability.

Various adhesives may be used, the fundamental requirements being that the adhesive is biocompatible for implant use and that a sufficient amount of adhesive is used between the porous PTFE layers to render the resulting laminate carvable. Other suitable thermoplastic adhesives in sheet form may include some polypropylenes, polyethylenes, polyesters and polyamides. The sheet materials are not required to be continuous, that is, they may be porous or perforated sheets if it is desired to have adjacent sheets of porous PTFE in some degree of direct contact, for example to allow tissue to grow through adjacent layers of the porous PTFE. Further, it is not required that the adhesive be a thermoplastic sheet material. For example, a layer of viscous silicone medical-grade adhesive (polydimethylsiloxane) may be applied between layers of porous PTFE and allowed to cure. One such adhesive is Rehau Raumedic SI1511 (Germany and Placentia, Calif.). It is believed that the use of higher durometer silicones will allow the laminate to achieve carvability with the use of a thinner adhesive layer.

The preferred porous PTFE for use in making the carvable implant material is porous expanded PTFE made as taught by U.S. Pat. Nos. 3,953,566; 3,962,153 and 4,187,390. These materials may be provided with other fillers such as carbon, if desired, as taught by U.S. Pat. No. 4,096,227. Preferred fibril lengths for porous expanded PTFE used to construct the present invention range from about 5 to 150 microns. Generally, a longer fibril length allows for faster tissue ingrowth to more quickly stabilize the implant at the intended location. Longer fibril lengths allow for an increased amount of tissue attachment which can be undesirable if it should be necessary to subsequently remove an implant with minimal trauma to surrounding tissue. It is believed that fibril lengths of about 10–25 microns provide the best compromise between rapid tissue ingrowth following implantation and subsequent retrieval of an implant with minimal trauma. Different fibril length sheets and/or different sheet thicknesses may be used for the exterior and intermediate layers if desired. Different fibril length sheets may be used on opposing exterior surfaces if desired.

The fibril length of porous expanded PTFE that has been expanded in a single direction is defined herein as the average of ten measurements between nodes connected by fibrils in the direction of expansion. Ten measurements are made in the following manner. First, a photomicrograph is made of a representative portion of the sample surface, of adequate magnification to show at least five sequential fibrils within the length of the photomicrograph. Two parallel lines are drawn across the length of the photomicrograph so as to divide the photograph into three equal areas, with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. The ten measurements obtained by this method are averaged to obtain the fibril length of the material.

For a porous, expanded PTFE material that has been expanded in more than one direction, the fibril length is estimated by examining a representative photomicrograph of the material surface and comparing fibril lengths as described above in a manner that represents the various direction orientations of the fibrils.

Figure 2:
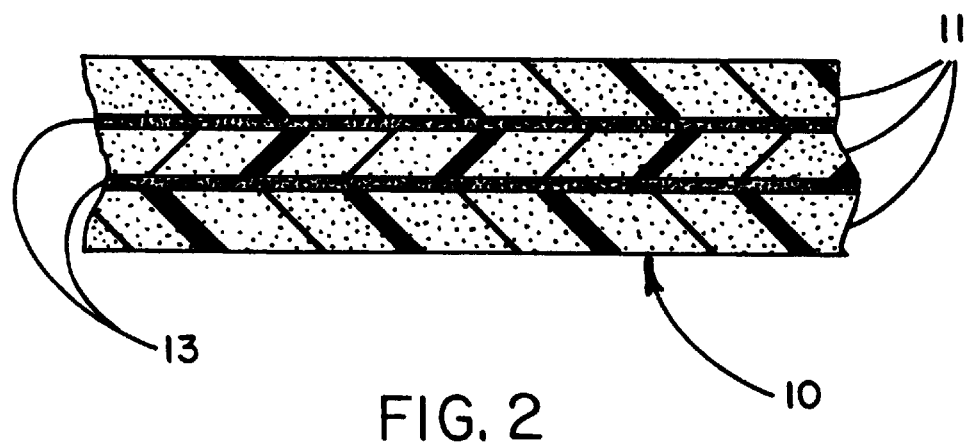
FIG. 2 describes a cross section of the implant material showing three layers of porous PTFE sheet material wherein the adjacent layers of the porous PTFE sheet material are laminated together by an adhesive.

As shown by FIG. 2, the carvable implant material preferably comprises at least three porous PTFE sheets 11 laminated by an adhesive 13 between adjacent layers. Where the adhesive is FEP sheet material, it has been found that continuous, unperforated FEP sheets of about 0.025 mm thickness used between porous expanded PTFE sheets of about 1.0 mm thickness and about 20–25 micron fibril length provide for good carvability. FEP sheets of about 0.012 mm thickness used with the same porous expanded PTFE sheets provide somewhat reduced stiffness for purposes of carvability. Likewise, FEP sheets of about 0.05 mm thickness used with the same porous expanded PTFE sheets result in a slightly stiffer laminate that was still easily carvable.

Figure 3:
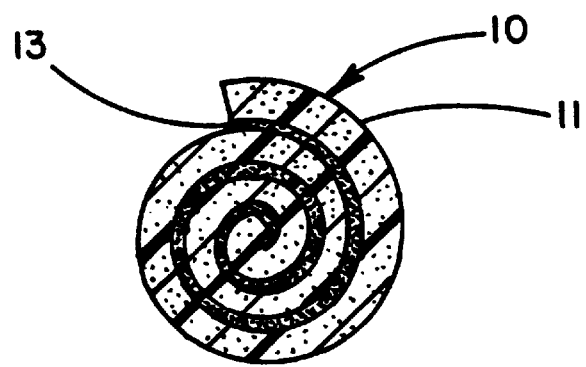
FIG. 3 describes a cross section of the implant material showing a single layer of porous PTFE sheet material in the form of a roll wherein adjacent layers of the roll are laminated together by an adhesive.

As described by FIG. 3, a carvable implant material may be formed from a single porous PTFE sheet 11 and a single adhesive sheet 13 by rolling the porous PTFE and adhesive sheets into the form shown having a spiral cross section. Although only a single porous PTFE sheet is used, the rolled single sheet forms, as viewed in cross section, the at least two layers of porous PTFE adhered by an adhesive and is therefore within the scope of the present invention.

In an alternative embodiment, it has been found possible to make a cork-like material from a plurality of discrete pieces of porous PTFE adhered together by an adhesive. The discrete pieces are preferably made by shredding sheets or other forms of porous PTFE into many small, irregularly shaped pieces. The pieces may be as small as about 1 mm across or smaller. The discrete pieces are mixed with an adhesive which is preferably a thermoplastic adhesive such as FEP fine powder. The amount of adhesive is relatively small and should preferably represent less than 10 percent of the weight of the mixed adhesive and porous PTFE. The mixture is placed into a mold and compression is applied until the adhesive is cured. The amount of compression should be appropriate to bring adjacent discrete pieces of porous PTFE into contact with each other and the adhesive while substantially eliminating the air spaces between the adjacent discrete pieces. The amount of compression should not be so great as to substantially reduce the porosity of the individual discrete pieces of porous PTFE. If the adhesive requires heat, then it is necessary to heat the compressed mixture to above the melt point of the adhesive and then allow it to cool, after which the compression is released and the resulting cork-like material is removed from the mold. Due to the presence of the adhesive, the cork-like PTFE material is carvable. If an adequately biocompatible adhesive is used, the cork-like PTFE material can be expected to serve as a carvable implant material.

In a variation of this embodiment, the mold may be lined with a sheet or tube of porous PTFE material after which shredded porous PTFE is placed into the cavity of the liner mold. The result is a cork-like material having an exterior covering of the tube or sheet of porous PTFE which was used to line the mold.

The carvability of various samples of the present invention was found to correlate well with the hardness of the samples as measured at room temperature (about 23° C.) by the method of ASTM D2240-91 using a Shore Durometer Type 0 with a Shore model CV-71200 Conveloader (Shore Instrument Co., Freeport, N.Y.); all durometer readings used herein in the specification and in the claims are according to this method. This durometer uses a hemispherical indenter of 1.2 mm radius. Samples tested by this method are required to be at least 6 mm in thickness. Two or more samples may be stacked if necessary to achieve the minimum 6 mm thickness. Five durometer readings were taken at five different points on each sample; these five readings were averaged with the resulting average taken as the representative hardness value of the sample. Samples having a mean durometer reading of at least 40 were found to be adequately stiff and hard to be carvable when carved with a scalpel blade. Samples having mean durometer readings of 50 to 60 were found to be preferred. Thickness measurements were the average of three or more measurements with a set of measuring calipers having an electronic digital readout.

EXAMPLES 1 mm thick GORE-TEX® Soft Tissue Patch (5.0 cm×10.0 cm, Part No. 1405010010, W. L. Gore & Associates, Inc., Flagstaff, Ariz.) was used as the porous PTFE sheet material. Eight layers of this material were stacked alternately with 0.025 mm thick non-porous sheets of FEP. The resulting stack was placed into a restraint fixture that gripped the edges of the stack in such a manner that shrinkage of the porous PTFE during the subsequent heating procedure was prevented. Compression was applied to the opposing surfaces of the stack in the amount of 2.4 g/cm². The stack was placed into an air convection oven set at 360° C. for a period of 35 minutes, removed from the oven and allowed to cool to about room temperature at which time the compression was removed and the resulting laminated stack was removed from the restraint fixture. The thickness of this laminated stack was 7.5 mm. The average of five durometer readings taken at five different points on the surface of the laminated stack was 72. This first example was easily carvable with a sharp scalpel blade.

For comparison, a control stack of 8 layers of the 1 mm thick GORE-TEX Soft Tissue Patch was assembled without the alternate adhesive sheet layers. Five durometer readings of this stack averaged 33. When held in compression under finger pressure, the stack was not practically carvable with a scalpel blade.

A second inventive sample was made in the same manner as the first except that 0.012 mm thick FEP sheet material was used in place of the 0.025 mm thick non-porous FEP sheet. This sample when completed was 7.5 mm thick; the average of the five durometer readings was 70. This second sample was also easily carvable with a sharp scalpel blade.

A third example was made in the same manner as the first except that 0.037 mm thick non-porous polypropylene sheet material was used between the adjacent layers of porous PTFE in place of the 0.025 mm thick FEP sheet material. The oven was set at 190° C. for this sample until the center of the sample reached a temperature of 180° C. as indicated by a thermocouple placed into the center of the stack when it was laid up. The thickness of the completed sample was 7.5 mm; the five durometer readings averaged 59. This third example was also easily carvable with a sharp scalpel blade.

A fourth example was made by adhering the eight layers of GORE-TEX Soft Tissue Patch material together with a layer of Dow Corning Silastic® Medical Adhesive Type A. A layer of this adhesive of about 0.5 mm thickness was applied between the adjacent layers of porous PTFE. Compression was applied to the resulting stack in the amount of 2.4 g/cm². The stack remained under compression overnight while the silicone adhesive cured at room temperature. The finished thickness of this sample was about 11.6 mm. The average of the five durometer measurements made on this sample was 44. The sample was carvable with a scalpel blade, although there was more resistance to the blade than with the first three samples. This was believed to be due to this sample being softer and less rigid and also due to drag on the scalpel blade caused by the presence of the silicone adhesive.

A fifth example was made in the same fashion as the first example except that an alternative form of porous expanded PTFE was used in place of the GORE-TEX Soft Tissue Patch material. For the alternative material, a length of 24 mm inside diameter GORE-TEX® Vascular Graft (W. L. Gore & Associates, Inc., Flagstaff, Ariz.) was slit longitudinally (parallel to the longitudinal axis of the graft) to create a sheet which was then cut into eight individual pieces of approximately 10 cm length. GORE-TEX Vascular Grafts are provided with an exterior layer of helically-wrapped porous PTFE film; this film was removed from each individual piece. The eight pieces were then stacked alternately with 0.025 mm thick non-porous sheets of FEP. The porous expanded PTFE sheets were stacked so that the longitudinal axis of the tube from which each sheet had been cut was oriented in a parallel direction for all eight sheets. It is anticipated that, because the vascular graft from which the sheets had been cut had been made by stretching the tube only in the direction of the longitudinal axis of the tube, a stack of sheets with more directionally uniform strength properties may be made by stacking each porous expanded PTFE sheet of this type with the longitudinal tube axis oriented perpendicular to that of the previous sheet. Finally, the stack was compressed and heated as described for the first example. The five durometer readings averaged 67.

Figure 4:
FIG. 4 is a photomicrograph (x15) of the cork-like embodiment of the present invention.

A sixth example was made in the form of the previously described cork-like material. A quantity of GORE-TEX Vascular Grafts of various lengths and diameters were reduced to small, discrete pieces of porous expanded PTFE by shredding in a Nelmor, Inc. shredding machine (model No. RG810M1, North Uxbridge, Mass.). The resulting discrete pieces of porous expanded PTFE were typically of irregular shape and of about 1 mm across their largest dimension. The discrete pieces ranged in size from less than 1 mm to about 4 mm. The adhesive used to subsequently adhere the discrete pieces of porous expanded PTFE was made from DuPont Teflon FEP 120 Aqueous Dispersion. A quantity of FEP fine powder was made by dipping a small paintbrush into the Teflon FEP 120 Aqueous Dispersion and allowing it to dry onto the bristles of the brush. The resulting FEP fine powder was collected from the brush. A mixture was then formed from 40.04 g of discrete pieces of porous expanded PTFE and 2.17 g of FEP fine powder. The mixture was placed into a cup-shaped mold having a flat bottom and a circular transverse cross section of about 33 mm diameter. A 365 g cylindrical weight that fit into the bore of the cup-shape mold was placed on top of the mixture lying in the bottom of the cup-shaped mold. An additional compressive force of about 225 kg was applied from a direction parallel to the longitudinal axis of the cup-shaped mold using a hand press for a period of about one second. The weighted mold was then placed into an air convection oven set at 345° C. for a period of 45 minutes, after which it was removed and allowed to cool to about room temperature. The weight was then removed from the mold, allowing the resulting cylindrical sample of cork-like porous expanded PTFE to also be removed from the mold. The resulting sample was of 33 mm diameter and 14 mm length and had a density of about 1.3 g/cc, in comparison to the density of solid, non-porous PTFE which has a density of about 2.2 g/cc. Five durometer readings of this sample averaged to 56. The sample was easily carvable with a scalpel blade. A photomicrograph (x 15) of the surfaces of a piece cut from this sample is shown by FIG. 4.

We claim:

1. A carvable implant material, comprising at least three sheets of porous polytetrafluoroethylene sheet material arranged to create a stack of adjacent layers of porous polytetrafluoroethylene sheet material, wherein the adjacent layers are adhered together by a thermoplastic adhesive that renders the porous polytetrafluoroethylene adequately rigid for carving and wherein said carvable implant material has a durometer reading of at least 40.

2. A carvable implant material according to claim 1 wherein the thermoplastic is a sheet material.

3. A carvable implant material according to claim 1 wherein the thermoplastic is a thermoplastic fluoropolymer.

4. A carvable implant material according to claim 3 wherein the thermoplastic fluoropolymer is fluorinated ethylene propylene.

5. A carvable implant material according to claim 4 wherein the fluorinated ethylene propylene is a fluorinated ethylene propylene dispersion.

6. A carvable implant material according to claim 4 wherein the fluorinated ethylene propylene is a sheet material.

7. A carvable implant material according to claim 1 wherein the porous polytetrafluoroethylene is porous expanded polytetrafluoroethylene having a microstructure of nodes interconnected by fibrils.

8. A carvable implant material according to claim 7 wherein the thermoplastic adhesive is a sheet material.

9. A carvable implant material according to claim 7 wherein the thermoplastic is a thermoplastic fluoropolymer.

10. A carvable implant material according to claim 9 wherein the thermoplastic fluoropolymer is fluorinated ethylene propylene.

11. A carvable implant material according to claim 10 wherein the fluorinated ethylene propylene is a fluorinated ethylene propylene dispersion.

12. A carvable implant material according to claim 10 wherein the fluorinated ethylene propylene is a sheet material.

13. A carvable implant material according to claim 1 wherein the carvable implant material has a durometer reading of at least 50.

14. A carvable implant material according to claim 7 wherein the carvable implant material has a durometer reading of at least 50.

15. A carvable implant material according to claim 10 wherein the carvable implant material has a durometer reading of at least 50.

* * * * *